United States Patent [19]

Lange

[11] 4,391,920

[45] Jul. 5, 1983

[54] POROSE, PULVERFORMIGE POLYMERTEILCHEN

[75] Inventor: Wolfgang Lange, Obernburg, Fed. Rep. of Germany

[73] Assignee: Akzo NV, Arnhem, Netherlands

[21] Appl. No.: 283,675

[22] Filed: Jul. 15, 1981

[30] Foreign Application Priority Data

Jul. 15, 1980 [DE] Fed. Rep. of Germany ....... 3026688

[51] Int. Cl.³ ............................................... C08J 9/26
[52] U.S. Cl. ..................................... 521/61; 264/140;
521/56; 521/64; 521/94
[58] Field of Search ....................... 521/61, 56, 94, 64;
264/140

[56] References Cited

U.S. PATENT DOCUMENTS

| 2,819,981 | 1/1958 | Schornstheimer | 521/61 |
| 3,591,524 | 7/1971 | Erickson | 210/924 |
| 3,607,793 | 9/1971 | Mahlman | 521/61 |
| 3,681,237 | 8/1972 | Orban | 521/55 |
| 3,888,766 | 6/1975 | de Young | 521/54 |
| 4,187,187 | 2/1980 | Turbeville | 210/924 |

Primary Examiner—Morton Foelak
Attorney, Agent, or Firm—Michael J. Striker

[57] ABSTRACT

The invention relates to a process producing porous powdery polymer particles. A homogeneous mixture having two components minimum, one a meltable polymer, the other fluid inert to the polymer, both forming a system having a range of complete miscibility and a miscibility gap are introduced to a bed of solid-substance particles, then cooling the mixture to below solidification of the polymer and comminuting the obtained cake-like mass. The polymer is separated then from the inert fluid and solid-like substance particles.

14 Claims, No Drawings

POROSE, PULVERFORMIGE POLYMERTEILCHEN

The invention relates to porous, powdery polymer particles, having a large internal surface accessible externally, to processes for their production as well as to their use.

It is known how to produce polymers, such as, f.i. polypropylene, with porous structure, particularly in the shape of compact structures such as panels, but also in the shape of films, filaments and hollow filaments. U.S. Pat. No. 3,607,703, f.i., describe a process by which, proceeding from small polypropylene particles of a size from approximately 0.02 to 0.5 $\mu$m and dissolving these in hydrocarbons, porous films may be obtained if cooling is performed at a rate of less than 100° C. per minute.

That process, however, is not usable for the production of porous, powdery polypropylene. Considerable difficulties will arise if it is attempted to transform porous structures as obtained by the doctrine of U.S. Pat. No. 3,607,793 into powdery state by means of comminution. On being ground, for instance, the material will, respectively, become viscous or begin to melt. A perfect, porous and powder-like product can also not be obtained by intensive cooling, since the structures will be crunched and ruptured during the grinding process. Also, no powder with favorable granulate-size distribution can be obtained in this manner.

Also, compact polymer masses with porous structure, as described in DE published application No. 2,727,745, can be pulverized in this manner only under difficulties and will yield a powder with unsatisfactory properties in many respects.

Size reduction under liquid oxygen will still not yield powders with fully satisfactory properties. Firstly, operating with liquid oxygen is costly, as it is energy-intensive and the generation of gas in large quantities, caused by evaporating nitrogen is noisome. Finally, the formation of fibrous edges at the surfaces where the particles were cut or broken, will exert an unfavorable effect upon the properties of the powder, f.i. its free-flowing qualities and cannot be avoided even by such intensive cooling as obtainable by the use of liquid oxygen.

Porous, powdery substances may be used in the most different fields, f.i. in adsorption, as additives or fillers, or similar. The need exists, therefore, for such porous substances, particularly such with improved properties and, also, for appropriate production processes.

The objective of the invention is, therefore, to make available porous, powdery polymer particles of suitable granule shape and size distribution, having a large internal surface accessible from the exterior, a uniform pore structure and good free-flowing qualities. The objective of the invention is further an improved process for the production of such polymer particles, which, in particular, should allow economical and simple production. The objective of the invention is, still further, to make evident particularly advantageous applications for such polymer particles, especially as carriers of substances for long-term release and having improved long-term effects.

This objective is attained by a process for the production of powdery, porous polymer particles, characterized by the introduction into a bed of solid-substance particles at a temperature above the segregating temperature, of a homogenous mixture having a minimum of two components, one component therein being a meltable polymer and the other component a fluid inert to the polymer, both components forming a binary system which has in its liquid phase a range of complete miscibility and also a range with a miscibility gap, by subsequent cooling said mixture to a temperature below the solidification temperature of the polymer in the mixture, by comminution of the cake-like mass as obtained and by separation of the polymer substance from the inert fluid and solid-substance particles.

Preferably, use is made of a solid-substance-particle bed of particles with a size from 50 to 5000 $\mu$m. Very suitable is a solid-substance-particle bed from glass beads. Salt may also be used as solid-substance particles, particularly sodium sulfate; the sodium sulfate will preferably be of a granulation from 50 to 400 $\mu$m.

According to the invention, use is preferably made of polymer particles from polypropylene. NN-bis-(2-hydroxyethyl)-hexadecylamine may be used herein as inert fluid.

When using glass beads as solid-substance particles, the cake obtained may first be extracted, then comminuted and the polymer particles be separated by reason of the different densities. Separation may, for instance, be effected by hydraulic separation.

It is practicable, first to comminute the cake obtained and perform extraction only thereafter; a reverse mode of operation is likewise practicable.

In a particularly advantageous embodiment of the invention, the cake as obtained is simultaneously being comminuted and subjected to extraction.

In some instances, it may even be practicable to subject the cake as obtained to simultaneous extraction, comminution and detaching of the solid-substance particles, so that the polymer particles will remain.

After separation of the polymer particles these may be gradated, into granule-size fractions by screening.

The objective of the invention are, yet further, porous, powdery polymer particles with apparent density from 0.1 to 0.6 g/cm$^3$, an externally accessible internal volume of more than 50%, preferably 70%, and a granule size from 50 to 700 $\mu$m, preferably 50 to 100 $\mu$m.

The particles as per invention are suitable for separation of hydrophobic substances from aqueous systems, particularly for separation of oil; they may, in an advantageous manner, also be used for the adsorption of fluids, particularly as oil adsorbent.

They are, furthermore, suitable as additives to coating media, particularly protective coating media.

They may, also be used, particularly favorable, as carriers of substandes for long-term release, with application in agriculture, forestry and also in horticulture, meriting special note.

They are, furthermore, chargeable with odorants, such as sexual attractants for insects.

A still further, very advantageous application is using the porous, powdery polymer particles as additives to concrete.

Production of the powdery, porous polymer particles may be made generally in the following manner.

Initially, a homogeneous liquid mixture is prepared by heating of a suitable polymer and an inert fluid. Polypropylene is particularly suitable as polymer.

Additional suitable polymers can be taken from DE published application No. 2,737,745, wherein are also listed suitable inert fluids. This corresponds to U.S. Pat.

No. 4,247,498, which is hereby incorporated by reference.

The homogeneous mixture is then introduced into a suitable bed of solid-substance particles. This may be effected, f.i. by constructing a solid-substance-particle bed over a groove, with use of a supporting filter plate being recommended in given instances. The solid-substance-particle bed will suitably be covered with a perforated plate serving to prevent the said bed from being stirred up during processing.

The melt is then poured onto this solid-substance-particle bed; application of a vacuum will allow enhancing penetration by the mixture. The solid-substance-particle bed is being heated to a temperature above the segregation temperature of the system used herein. Charging is terminated as soon as the solid-substance-particle bed has been saturated with the melt; after allowing to cool, a cake of friable consistency will be obtained.

This will then be comminuted and treated with an extractant in which the inert fluid is soluble.

The solid-substance particles and the porous polymer particles are then separated. This may be effected either mechanically or by a chemical method.

In particular instances, it will be possible to use an extractant which will simultaneously also effect dissolving of the solid-substance particles.

It is possible, f.i. when using NN-bis-(2-hydroxyethyl)-hexadecylamine as inert fluid, to use acidulated water for extraction and detaching of the solid-substance-particle bed, provided said bed consists of a soluble substance, such as, f.i., sodium sulfate.

The process may be performed in a continual manner by, f.i. simultaneously charging the heated tube with metered quantities of solid-substance-particles and the homogeneous mixture. The material is then moved through the tube, with the temperature being lowered while the mixture is passing through the tube. After discharging from the tube, the mass is comminuted and extracted. The extractant may be separated by filtration. The extracted mass is subsequently process with, f.i. water or another medium, and dried.

The polymer particles obtained may, if required, furthermore also be separated into individual particle fractions by air separation or screening.

It was found to be particularly unexpected, that porous, powdery polymer particles could be obtained in a particularly advantageous, economical manner by the process according to this invention. The polymer particles are distinguished by a favorable granule shape, have good free-flowing properties and a very large internal pore volume accessible from the exterior, as well as very large internal surfaces accessible from the exterior.

It is practicable to control also the granule size of the polymer powder obtained, by suitably selecting the solid-substance-particle bed, particularly by using particles of appropriate granule size. It was found to be particularly unexpected that, according to the invention, a porous polymer powder became available, showing improved long-term release. The invention had rendered practicable the obtaining of polymer particles with different degrees of close-poredness or, respectively, open-poredness, i.e. areas with very small openings will, on one and the same particle, alternate with areas that have larger openings. A result thereof is that particles, when charged with substances for long-term release, will be releasing such substances over a longer time than is the case with particles where the entire surface is occupied by larger pores.

The particles according to invention are thus particularly suitable in applications as carrier of substances for long-term release in the field of agriculture, forestry, as well as in horticulture. They are readily sprayable.

It is also practicable to charge these particles with trace elements; they are also suitable as carriers for antifoulants, molluscides, insecticides, herbicides, fungicides, rodenticides, nematicides, algicides, repellents etc.

It was found particularly unexpected that the polymer particles according to invention could also be used as additives for concrete, with particles of granulation from approximately 50 to 70 $\mu$m being particularly suitable therefor. If these polymer particles are admixed in preferably small quantities to concrete, the concrete will display particularly suitable cold-weather characteristics. It is, above all, the feared formation of cracks which may develop in concrete being cured at low temperatures, that can be prevented or, respectively, reduced to a considerable extent.

Using the process according to invention, it is furthermore possible to control the porosity, i.e. the proportion of the pore volume in the particle, particularly by increasing the proportion of inert liquid in the homogeneous mixture. It is therefor, that, preferentially, mixtures will be used containing a minimum of 70% of the inert fluid and a maximum of 30% of polymers.

It was, furthermore, unexpected, that the powders, when used for instance in agriculture, will well adhere to plant leaves since, apparently due to their exterior structure, said powders will stick well to the surface areas of the plants. It is due to this reason to maintain a longer protective effect on plants.

The invention will be more closely explained by the following example:

EXAMPLE 240 g NN-bis-(2-hydroxyethyl)-hexadecylamine plus 60 g polypropylene pph 1050 (black 12, Hoechst AG) are heated to 260° C. in a glass flask with stirring. The melt of 260° C. is then decanted into a filter funnel (Buchner funnel) containing 900 g sodium sulfate heated to 240° C.

By application of a vacuum, the hot melt is siphoned into the salt layer. The melt cake will have cooled down after 2 hours and is then comminuted with the addition of ethanol, by grinding in a suitable mixer/blender for 2 minutes. The mixture thus obtained is then poured into a filter funnel. The sodium sulfate remaining on the filter is dissolved with water and thus separated from the powder. The dried powder is subsequently classified into individual fractions by a vibrating sieve. The powder can be characterized as follows:

Particle size:
Fraction 1: 400 $\mu$m (larger than)—2.05%
Fraction 2: 315 $\mu$m (larger than)—0.54%
Fraction 3: 200 $\mu$m (larger than)—5.40%
Fraction 4: 100 $\mu$m (larger than)—42.28%
Fraction 5: 50 $\mu$m (larger than)—39.70%
Fraction 6: 50 $\mu$m (smaller than)—10.03%

After determination of the apparent density, a porosity of 57% was computed for the fraction from 100 to 200 $\mu$m. The larger particles have a higher proportion of pore volume.

I claim:

1. Process for the production of powdery, porous polymer particles, characterized by the introduction into a bed of solid-substance particles at a temperature above the segregating temperature, of a homogenous mixture having a minimum of two components, one component therein being a meltable polymer and the other component a fluid inert to the polymer, both components forming a binary system which has in its liquid phase a range of complete miscibility and also a range with a miscibility gap, by subsequent cooling said mixture to a temperature below the solidification temperature of the polymer in the mixture, by comminution of the cake-like mass as obtained and by separation of the polymer substance from the inert fluid and solid-substance particles.

2. Process as per claim 1, characterized by using a solid-substance-particle bed of particles with a size from 50 to 5000 μm.

3. Process as per claim 1, characterized by using a solid-substance-particle bed of glass beads.

4. Process as per claim 1, characterized by using salt as solid-substance particles.

5. Process as per claim 4, characterized by using sodium sulfate as salt.

6. Process as per claim 5, characterized by using sodium sulfate with a granule size from 50 to 400 μm.

7. Process as per claim 1, characterized by using polypropylene as polymer.

8. Process as per claim 7, characterized by using polypropylene as polymer and NN-bis-(2-hydroxyethyl)-hexadecylamine as inert fluid.

9. Process as per claim 3, characterized by extracting the inert fluid from the cake obtained, comminuting the cake and separating the glass beads from the polymer particles by reason of their different densities.

10. Process as per claim 9, characterized by size-separation being effected by hydraulic separation.

11. Process as per claim 1, characterized by subjecting the obtained cake first to comminution and then to extraction.

12. Process as per claim 1, characterized by subjecting the obtained cake to simultaneously performed comminution and extraction.

13. Process as per claim 1, characterized by subjecting the obtained cake to simultaneously performed extraction, detaching of solid-substance particles and comminution of the cake.

14. Process as per claim 1, characterized by gradation of the polymeric, powdery porous particles into granule-size fractions by screening, ensuing subsequent to separation of the inert fluid and the solid-substance particles.

* * * * *

UNITED STATES PATENT AND TRADEMARK OFFICE
CERTIFICATE OF CORRECTION

PATENT NO. : 4,391,920
DATED : July 5, 1983
INVENTOR(S) : Wolfgang Lange

It is certified that error appears in the above—identified patent and that said Letters Patent is hereby corrected as shown below:

On the title page, the title should read:

--POROUS, POWDERY POLYMER PARTICLES--

Signed and Sealed this

Eleventh Day of September 1984

[SEAL]

Attest:

GERALD J. MOSSINGHOFF

Attesting Officer

Commissioner of Patents and Trademarks